(12) United States Patent
Yahiro et al.

(10) Patent No.: US 6,228,636 B1
(45) Date of Patent: May 8, 2001

(54) INCUBATOR

(75) Inventors: Kanji Yahiro; Akira Higuchi, both of Fukuoka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/401,040

(22) Filed: Sep. 21, 1999

(30) Foreign Application Priority Data

Sep. 21, 1998 (JP) .................................... 11-266178
Jun. 23, 1999 (JP) .................................... 11-176461
Jun. 23, 1999 (JP) .................................... 11-176462

(51) Int. Cl.[7] .................................................... C12M 1/00
(52) U.S. Cl. ........................ 435/303.1; 435/303; 312/43; 312/236; 600/22
(58) Field of Search .......................... 435/303.1, 303.2; 312/1, 35, 43, 236; 600/22

(56) References Cited

U.S. PATENT DOCUMENTS 4,892,830 * 1/1990 Findley et al. .................... 435/290

* cited by examiner

Primary Examiner—David A. Redding
(74) Attorney, Agent, or Firm—Ratner & Prestia

(57) ABSTRACT

An incubator includes (a) a housing, (b) a sample shelf holding at least one plate accommodating a sample, (c) a controller maintaining an environment inside of the housing at a given condition, (d) a first opening provided on the housing, (e) a first door for closing the first opening, (f) a second opening provided on the housing and smaller than the first opening and yet large enough for at least one plate being passed through, and (g) a second door for closing the second opening. This construction allows the incubator to minimize opening when the plate is taken out or restored during a test or a culture so that environment changes in the housing can be restrained. As a result, the incubator produces reliable data.

11 Claims, 9 Drawing Sheets

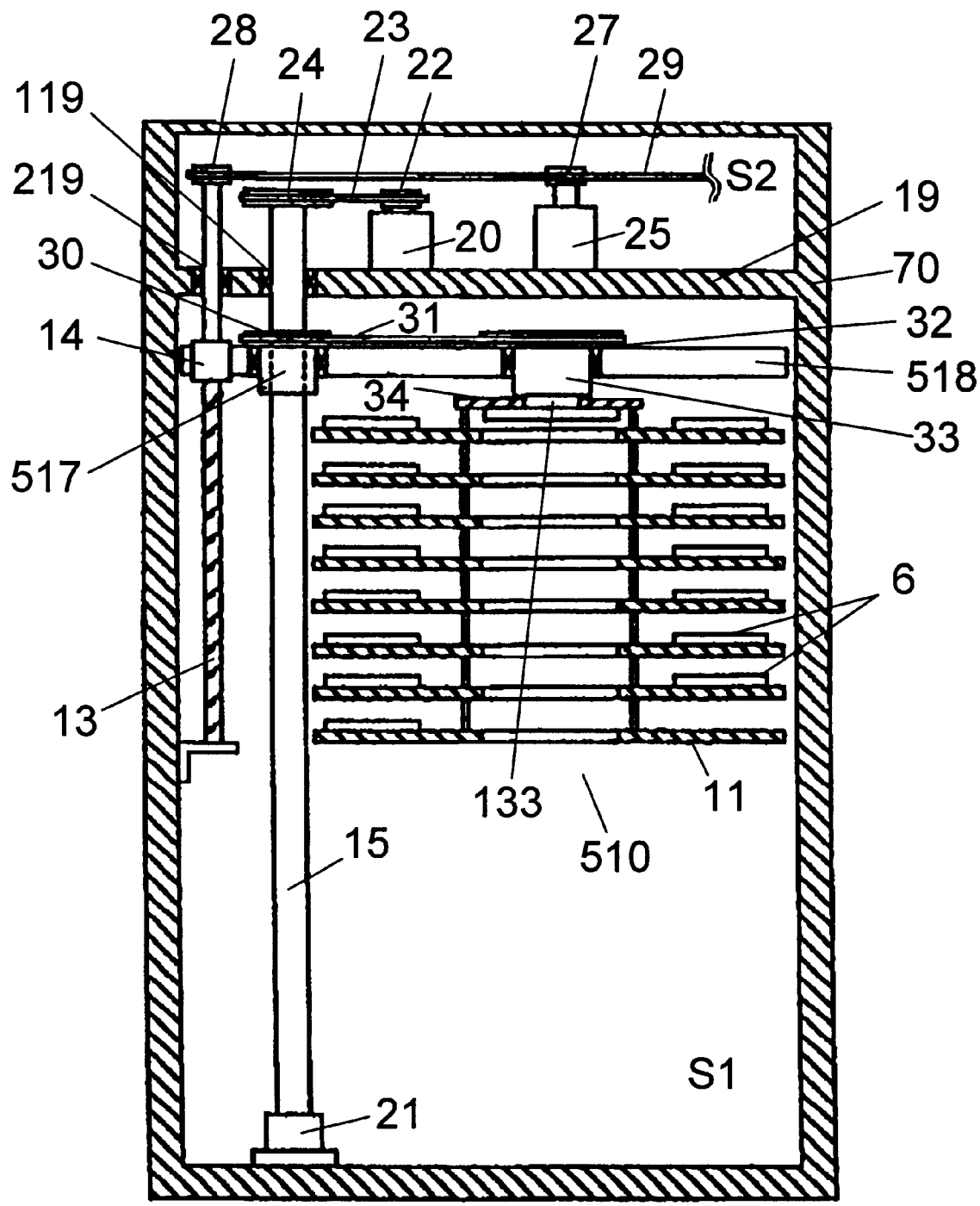

INCUBATOR

FIELD OF THE INVENTION

The present invention relates to incubators employed in culturing cells and microbes in the biochemical field.

BACKGROUND OF THE INVENTION

Incubators have been known as instruments employed in biochemical treatment such as culturing microbes or cells, as well as observing biochemical reactions. Incubators are the housings, where objective samples of culture or test are situated, equipped with functions maintaining a habitable environment for the samples such as a temperature and a humidity in the housings. Since a large number of samples are cultured or tested under the same environment, incubators in general accommodate a large number of samples.

It is frequently desirable to monitor biochemical treatment for an extended period of time, and thus the samples must be sequentially taken out from the incubator for routines such as analysis, observation and reagent distribution, then the samples are restored into the incubator. These routines must be practiced at a given interval. An opening is thus provided to the incubator so that samples can be taken out and restored. A large opening is provided to conventional incubators because this opening is used for various applications in addition to the purpose discussed above such as locating samples in the incubator, cleaning inside thereof and maintenance work.

However, every time the opening is opened at taking out and restoring the samples, gaseous atmosphere inside the incubator flows out and the open air flows in. As a result, the environment inside the incubator such as a temperature and humidity are changed. If the environment change exceeds a maximum tolerable limit, it lowers reliability of the culture or test result.

As such, the conventional incubator has an opening, which is frequently opened and closed, large enough to change the inside environment. This has left a problem of lowering reliability of culturing or testing the samples.

SUMMARY OF THE INVENTION

The present invention addresses the problem discussed above and aims to provide an incubator which maintains its inner environment and produces reliable data.

The incubator of the present invention comprises the following elements:

(a) a housing;
(b) a sample shelf disposed inside the incubator, and on the shelf at least one plate containing a sample is rested;
(c) a controller for maintaining an environment inside of the incubator at a given condition;
(d) a first opening formed on the housing;
(e) a first door for closing the first opening;
(f) a second opening smaller than the first one and formed on the housing, and through this opening at least one plate can travel; and
(g) a second door for closing the second opening.

The construction discussed above allows the incubator to minimize openings at taking out and restoring the plates during a test or a culture so that an environment change can be restrained. As a result, the incubator can produce a reliable data.

BRIEF DESCRIPTION OF THE DRAWINGS

FIG. 9 is a lateral cross section of the incubator shown in FIGS. 7 and 8.

DETAILED DESCRIPTION OF THE EXEMPLARY EMBODIMENTS

Exemplary embodiments of the present invention are demonstrated hereinafter with reference to the accompanying drawings.

Exemplary Embodiment 1

Figure 6:
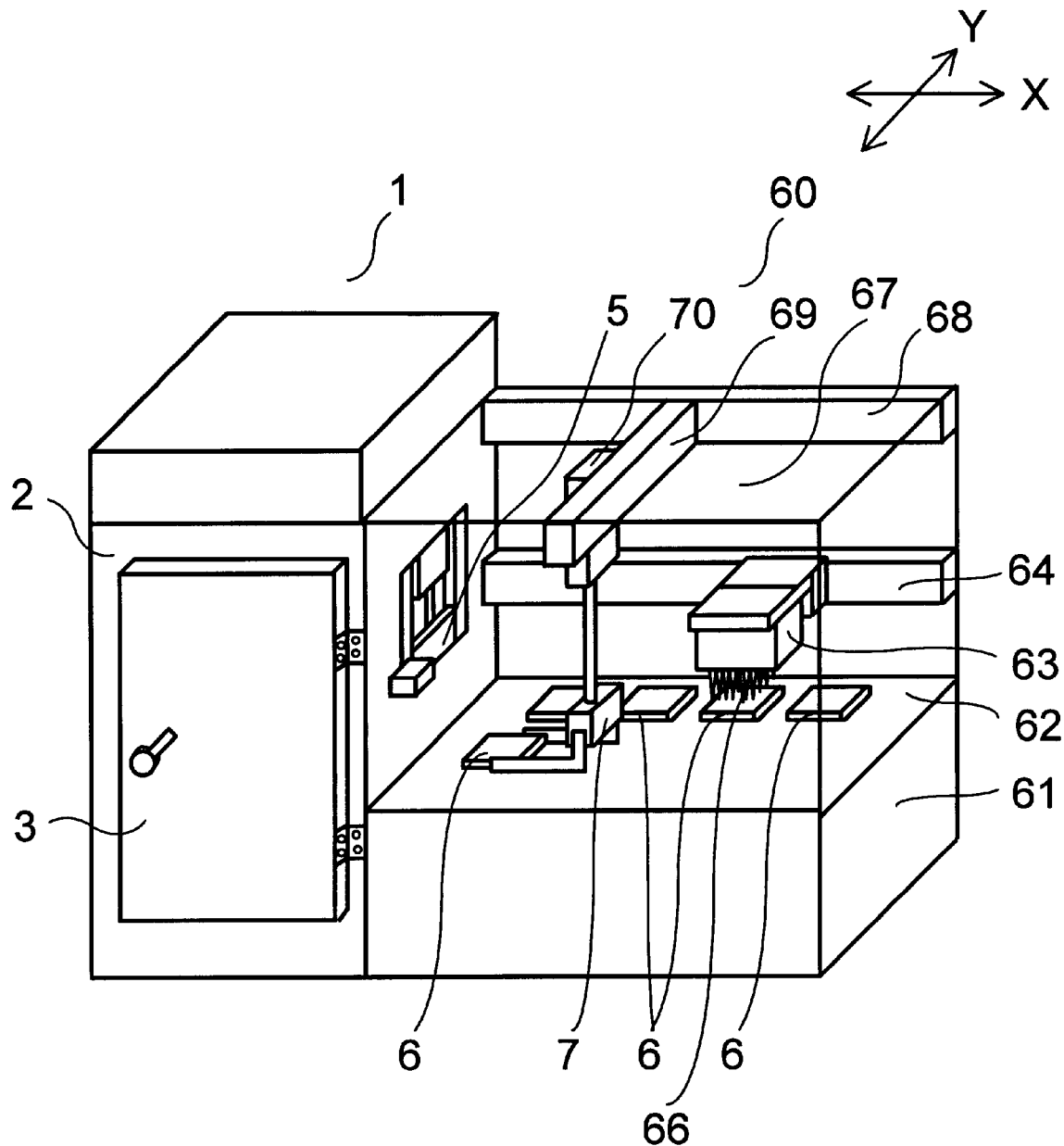
FIG. 6 is a perspective view of the same incubator and a distribution device.

An incubator and a distribution device combined with the incubator are demonstrated with reference to FIG. 6.

In FIG. 6, incubator 1 comprises box-type housing 2, and a first opening and its door 3 are provided on a front face of housing 2. Second opening 202 and its shutter 5 for opening and closing second opening 202 are provided on a lateral face of housing 2.

Distribution device 60 is equipped adjacent to the incubator. An upper face of base 61 of distribution device 60 is used as distribution stage 62, on which a plurality of plates 6 are situated. Plate 6 is equipped with a large number of wells that accommodate samples including biochemical materials. Above stage 62, X-axis table 64 is disposed, and a distribution head 63 is coupled to X-axis table 64. Beneath head 63, a large number of distributing chips 66 are mounted. X-axis table 64 is driven, whereby head 63 is moved above stage 62, and head 63 sucks one sample from one plate among plates 6 rested on stage 62. Head 63 then distributes the sample to other plates.

Above stage 62, plate transfer mechanism 67 is provided. Mechanism 67 comprises X-axis table 68, Y-axis table 69, Zθ-axis table 70 and moving head 7 coupled to table 70. Mechanism 67 is driven, so that head 7 clamps plate 6 rested on stage 62 and then brings plate 6 into incubator 1 through second opening 202. As such, taking out and restoring a sample from/into incubator 1 can be practiced through second opening 202 shown in FIG. 1.

An inner structure of the incubator is described hereinafter with reference to FIG. 1 through FIG. 4.

Figure 1:
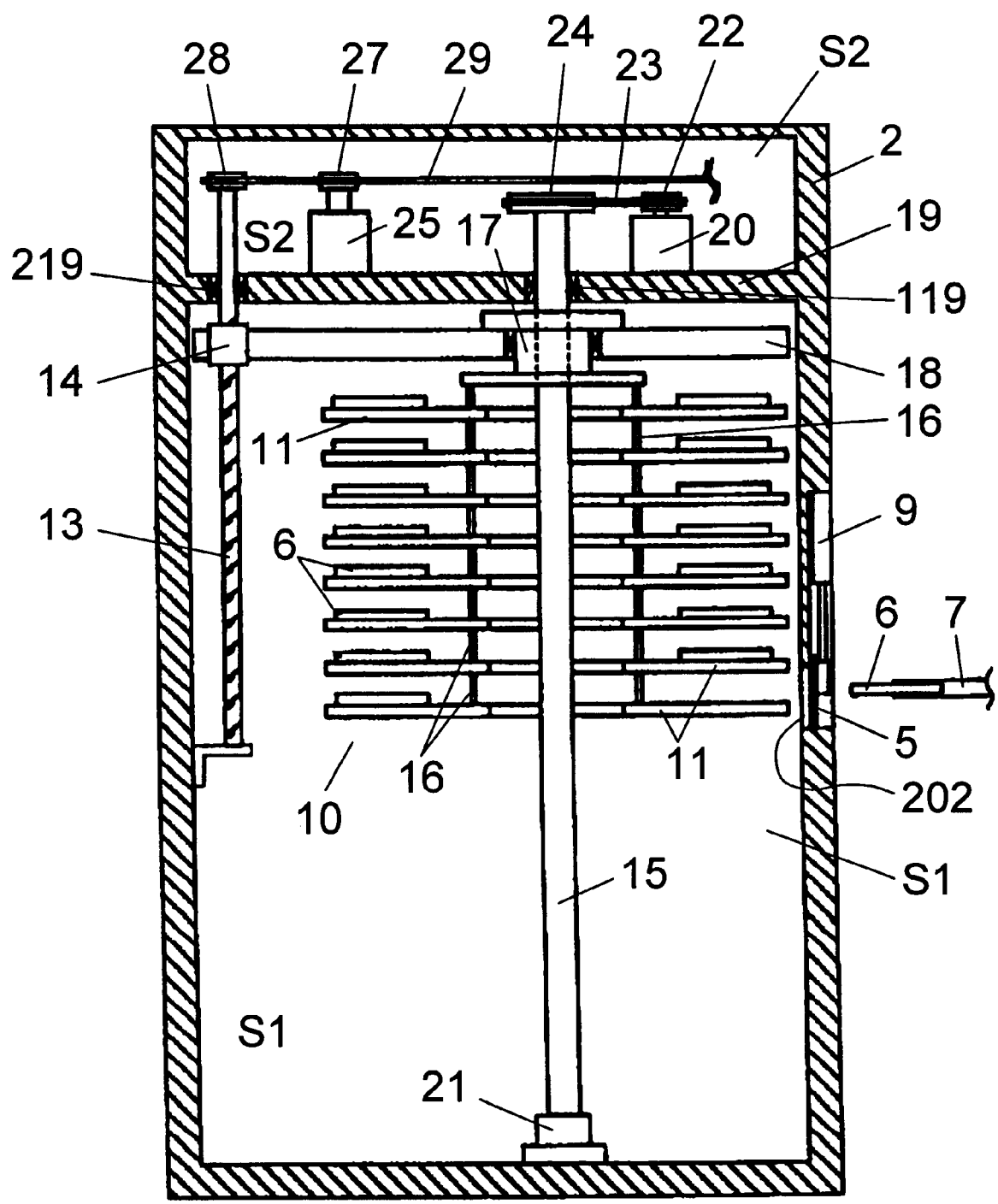
FIG. 1 is a lateral cross section of an incubator in accordance with a first exemplary embodiment.
Figure 2:
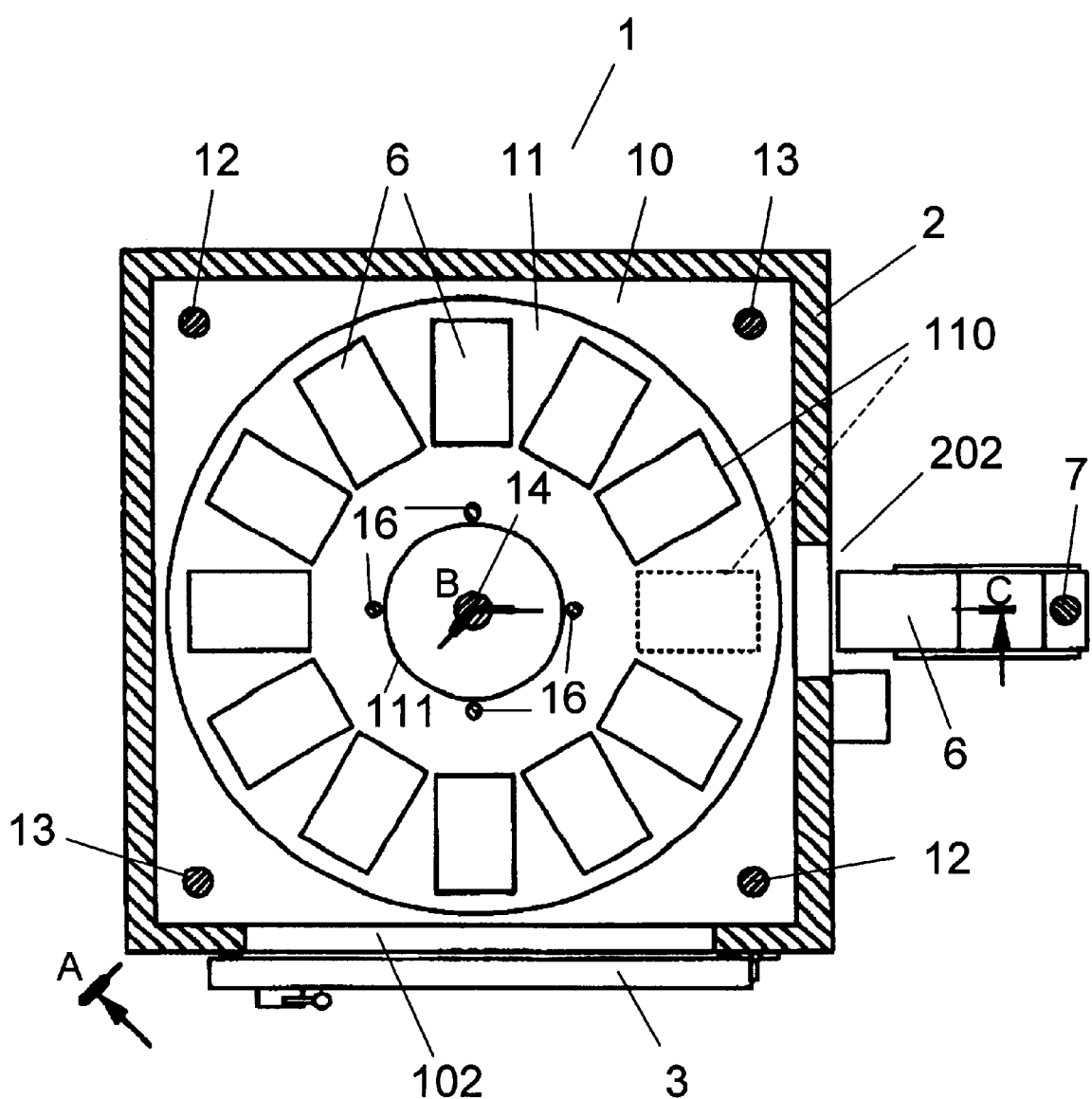
FIGS. 2 and 3 are plan cross sections of the incubator shown in FIG. 1.
Figure 3:
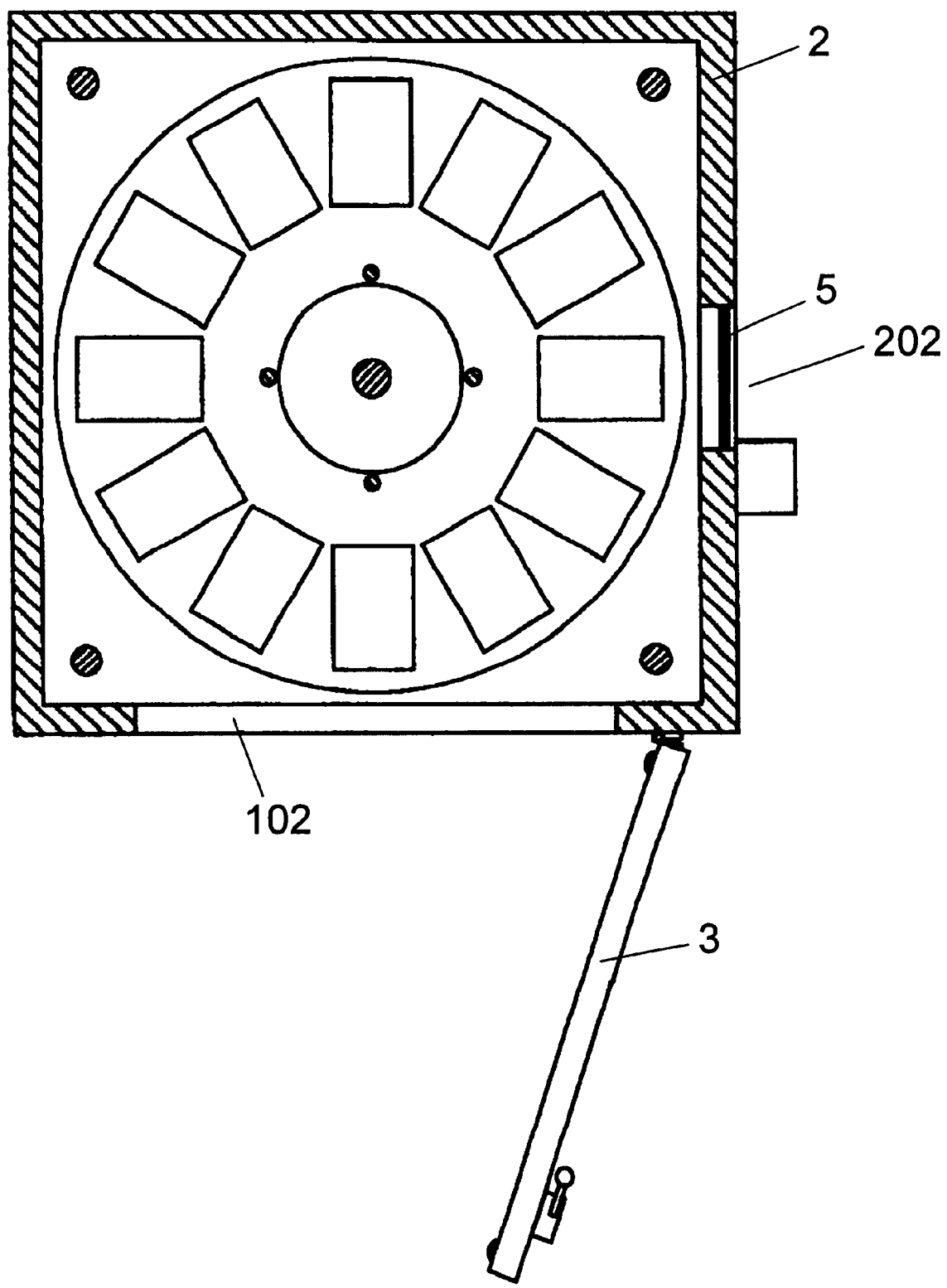

In FIG. 1 through FIG. 3, an outer frame of incubator 1 comprises housing 2 made of heat-insulating-wall. Housing 2 incorporates a water jacket (not shown), and the environment inside housing 2, such as a temperature, humidity, and density of $CO_2$, are maintainable at given levels by an environment controller (not shown).

On the front face of housing 2, first opening 102 is provided with door 3. On the lateral face of housing 2, second opening 202 is provided with shutter 5 vertically movable. Second opening 202 is as narrow as at least one plate 6 can travel through, and is used for taking out and restoring plate 6 from/to housing 2.

Shutter 5 is moved vertically by cylinder 9 which functions as a driver, and thereby opening or closing second opening 202. FIG. 3 illustrates a condition where door 3 is opened so that the inside of housing 2 can be seen through opening 102, and second opening 202 is closed by shutter 5.

Sample shelf 10 comprising a plurality of disc-type tables 11 assembled in series is disposed in housing 2. As shown in FIG. 2, at the center of tables 11, hole 111 is punched. On an upper face of table 11, a plurality of receptors 110 are radially prepared for receiving respective plates 6. Receptors 110 are labeled with their own numbers for a user or the controller to identify a specified receptor 110.

Figure 4:
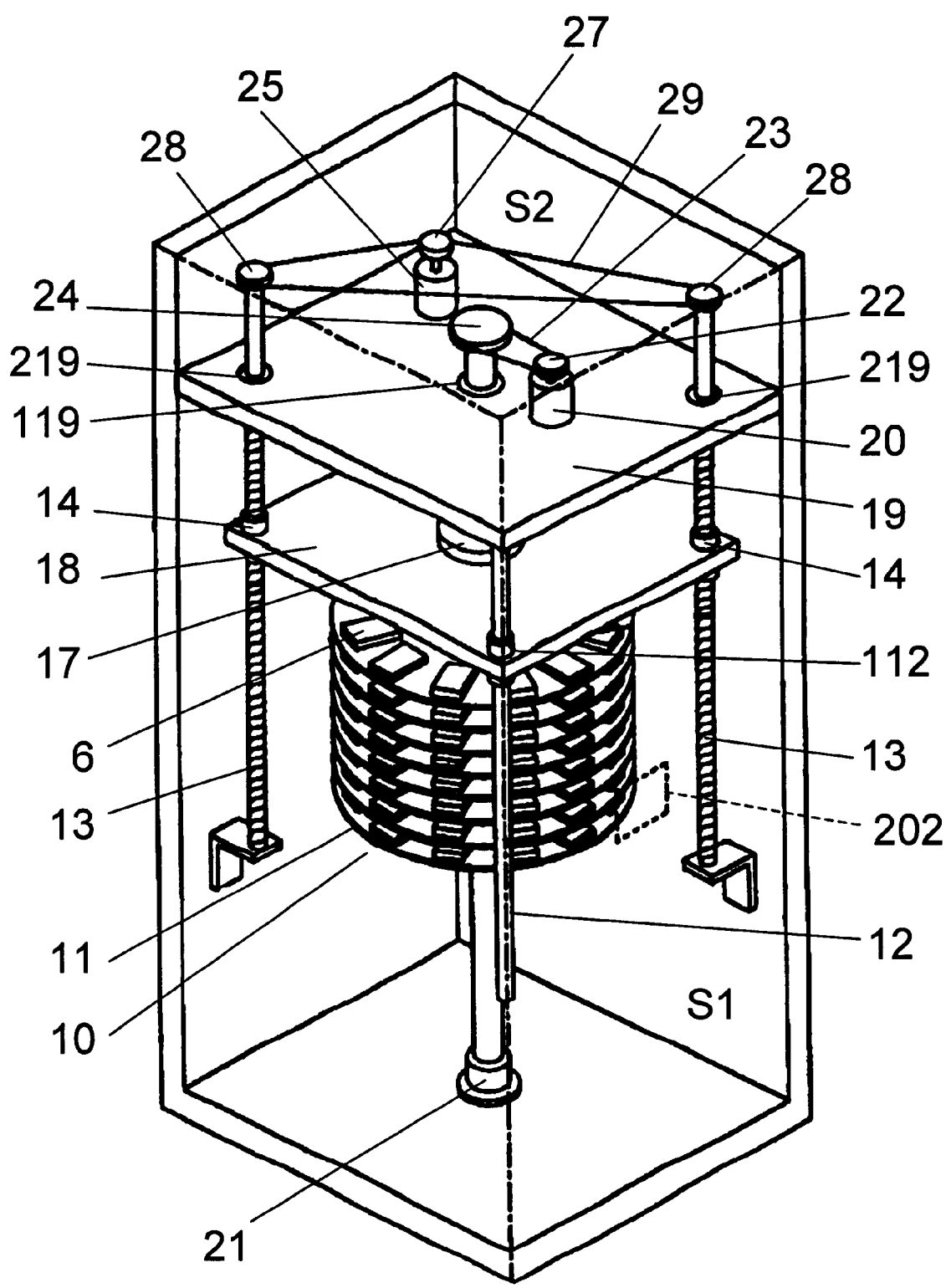
FIG. 4 is a perspective view illustrating an inside of the same incubator.

FIG. 1 is a lateral cross section taken on lines A☐ B☐C of FIG. 2. FIG. 4 is a perspective view showing the inside of the incubator.

As shown in FIG. 1 and FIG. 4, the inside of housing 2 is partitioned into two spaces, i.e. S1 and S2, by plane floor 19. The lower space S1 accommodates samples for biochemical treatment in a controlled environment. In the upper space S2, a driving mechanism for driving sample shelf 10 disposed in space S1 is provided. Space S2 is not necessarily shielded but is opened by eliminating the surrounding wall.

Shelf 10 comprises a plurality of tables 11 assembled vertically in series with link member 16. The upper most table is coupled to rotating body 17 with link member 16. Rotating body 17 is journaled by lift member 18. Through rotating body 17, spline shaft 15 vertically disposed extends in a slidable manner. A bottom of shaft 15 is journaled by bearing 21 disposed on base plate of housing 2. An upper section of shaft 15 is journaled by bearing 119 mounted in a shaft hole punched on floor 19, and protrudes into space S2. The upper section of shaft 15 is coupled to pulley 24.

R-axis motor 20 is disposed on the upper face of floor 19. Pulley 22 is coupled to a rotary shaft of motor 20. Pulley 22 is coupled to pulley 24 via belt 23. Thus driving of motor 20 results in rotating shaft 15, which is then transferred to rotating body 17, so that shelf 10 wheels together with shaft 15. This rotation driving mechanism, which rotates shelf 10 by rotating shaft 15, comprises motor 20, pulley 22, belt 23 and pulley 24.

On two diagonal positions of lift member 18, nut 14 is prepared respectively (FIG. 1 only shows one nut). Feed screws 13 are vertically engaged with respective nuts 14. An upper section of screw 13 is journaled by bearing 219 provided in a shaft hole on floor 19, and protrudes into space S2. An upper end of screw 13 is coupled to pulley 28.

Z-axis motor 25 is disposed on the upper face of floor 19. A rotary shaft of motor 25 is coupled to pulley 27, which is linked to pulley 28 via belt 29.

Lift member 18 is equipped with two sliders 112 (FIG. 4 only shows one slider.) Through these sliders 112, slide guide 12 extends respectively in a slidable manner. Up and down motion of lift member 18 is guided by guides 12 and sliders 112.

Driving motor 25 rotates screw 13, which results in lifting lift member 18. This lift driving mechanism, which lifts lift member 18 by rotating screw 13, comprises motor 25, pulley 27, pulley 28 and belt 29.

Up and down movement of lift member 18 is accompanied by the same movement of shelf 10. During the movement, shelf 10 is rotatable by shaft 15 regardless of a position of shelf 10. In other words, shelf 10 is movable by a combination of rotating and lift movements.

As such, the rotation driving mechanism and lift driving mechanism discussed above form a transfer mechanism for shelf 10. During this transfer operation, encoders (not shown) provided in R-axis motor 20 and Z-axis motor 25 generate pulse signals. The location of respective receptors 110 can be identified by counting the pulse signals.

The construction discussed above tells in short that spline shaft 15 is coupled to the rotation driving mechanism via bearing 119 disposed on floor 19, and screws 13 are coupled to the lift driving mechanism via bearing 219 disposed on floor 19.

This construction allows housing 2 to be partitioned into two spaces, i.e. the first space S1 where atmosphere of high temperature and high humidity usually prevails, and the second space S2 where driving mechanisms such as motors are disposed. The driving mechanisms can be thus separated and protected from the environment of high temperature and high humidity.

Figure 5:
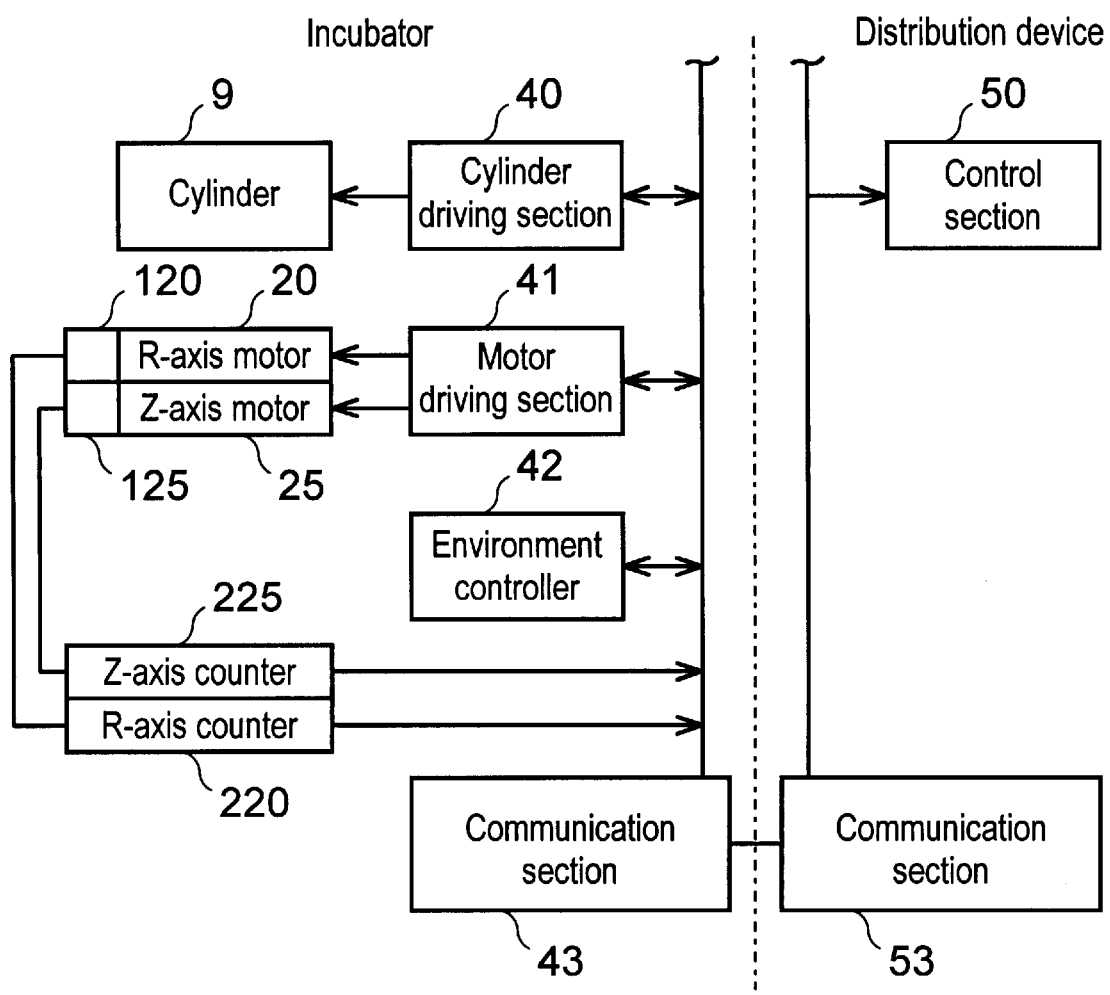
FIG. 5 is a block diagram illustrating a control system of the same incubator.

A control system of incubator 1 is demonstrated with reference to FIG. 5.

Cylinder driving section 40 drives cylinder 9 which raises or lowers shutter 5 for opening or closing second opening 202, through which the plates are taken out or entered. Motor driving section 41 drives Z-axis motor 25 which raises or lowers lift member 18 and R-axis motor 20, where motor 20 rotates shelf 10 and incorporates encoder 120. Encoder 120 outputs pulse signals embodying the rotation status of motor 20. These pulse signals are counted by R-axis counter 220. Motor 25 incorporates encoder 125, which outputs pulse signals embodying the rotation status of motor 25. These pulse signals are counted by Z-axis counter 225.

Numbers counted by counters 220 and 225 are referred to as information for identifying a position of receptor 110. In this embodiment, encoder 120, counter 220, encoder 125 and counter 225 jointly detect a position of shelf 10. Besides the encoders built in the motors, various detectors are available, e.g. a detector directly detects the position of shelf 10, or a detector outputs pulse signals by detecting the movements of shelf 10.

Environment controller 42 maintains the environmental condition such as a temperature, humidity and a density of $CO_2$ inside of housing 2. Communication section 43 transmits or receives signals necessary for controlling respective sections of incubator 1 Control section 50 is disposed in distribution device 60 which works in combination with incubator 1. Control section 50 controls operations of respective sections of incubator 1 via communication section 43 of incubator 1 and communication section 53 of distribution device 60 in the following manner.

Control section 50 instructs cylinder driving section 40 to open or close second opening 202 when plate 6 rested on receptor 110 is taken out from incubator 1. Control section 50 refers to numbers counted by counters 220 and 225, thereby identifying a position of receptor 110. For instance, the receptor positioned in front of opening 202 is specified its location with its number. Control section 50 instructs motor driving section 41 to position shelf 10 or to start an agitating operation.

Motor driving section 41 is controlled so that arbitrary receptor 110 can be positioned at a given location and shelf 10 can perform an agitating operation which is achieved by combining a lift and a rotating operations. This agitating operation lifts and/or rotates shelf 10 in order to agitate the atmosphere inside the first space S1☐ environment control room of incubator 1☐ so that a temperature and humidity can be even anywhere in S1. The positioning and agitating operations discussed above are selectively performed by an instruction from control section 50, which thus forms a controller of a mechanism transferring shelf 10.

An operation of the incubator used in the first exemplary embodiment and having a construction discussed above is demonstrated hereinafter.

Prior to a biochemical treatment, plates 6 is set inside incubator 1. Through this setting, plate 6 accommodating a given sample is placed at a given receptor 110 on table 11. During this setting operation, first opening 102 can be kept opening so that a wide area for access is maintained. A number of plates can be thus quickly placed at given receptors. When first opening 102 is kept opening, cleaning and maintenance work inside housing 2 can be also completed in an efficient manner.

After the setting of plates 6, door 3 is closed. Then environment controller 42 starts to operate, thereby maintaining the environment condition inside housing 2 at given levels. The biochemical treatment is then started according to an assay program of distribution device 60. During this treatment, plate 6 undergone a given time of culture is taken out from incubator 1 by moving head 7 (transfer mechanism). After undergoing an analysis and a distribution by the distribution device, plate 6 is restored into incubator 1 by head 7. This operation is repeated.

Plate 6 is taken out and restored from/to incubator 1 through second opening 202 provided on the wall which separates incubator 1 from the outside. An area of opening 202 is as narrow as such as one plate 6 just can travel through, and yet opening 202 is opened with shutter 5 automatically by controller 50 only when plate 6 must travel through opening 202. This mechanism thus allows incubator 1 to minimize disturbance to the environment, i.e. restraining flow-out of inner gaseous environment to the outside as well as flow-in of outside air into incubator 1.

Comparing with a conventional incubator which requires to open door 3 every time when plates 6 are taken out and restored, the incubator of the present invention can minimize changes of the environment inside the incubator so that it can maintain quality of biochemical treatment.

In the embodiment discussed above, second opening 202 is provided on a lateral side of housing 2; however, the opening can be formed on door 3.

During the biochemical treatment, sample shelf 10 is moved at given intervals so that atmosphere inside the incubator can be agitated. This agitating operation is achieved by combining the rotating and lifting operations applied to shelf 10. This agitating operation allows the gaseous environment within incubator 1□ having shelf 10 in a complicated shape with a number of tables 11□ to be agitated evenly in a narrow space between each table 11. Comparing with the conventional incubator which employs a ventilating fan, a remarkable agitating effect is produced in this embodiment. When the incubator of the present invention accommodates a large number of samples, respective samples are free from dispersion on treatment.

Exemplary Embodiment 2

Figure 7:
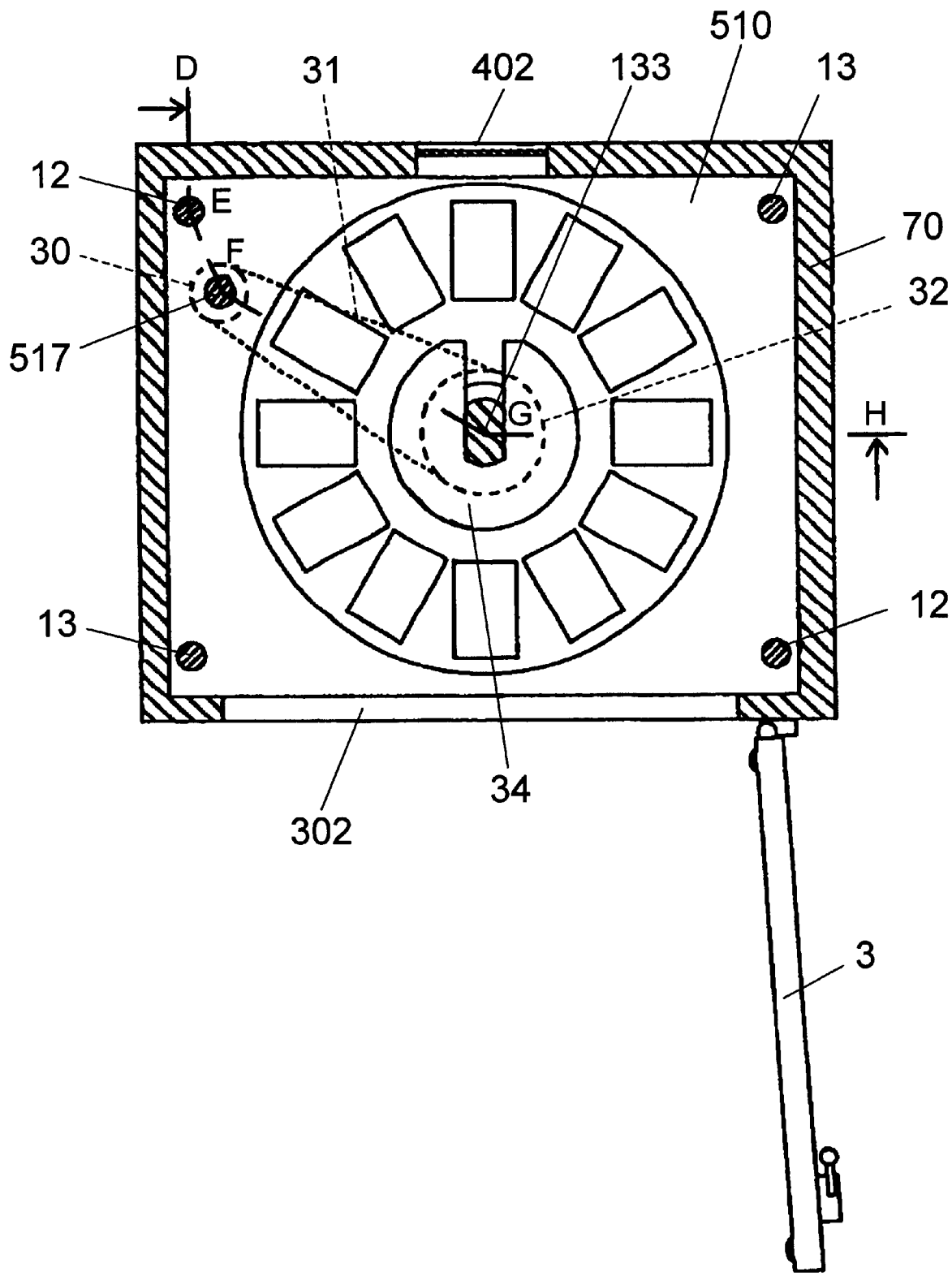
FIGS. 7 and 8 are plan cross sections of an incubator in accordance with a second exemplary embodiment.
Figure 8:
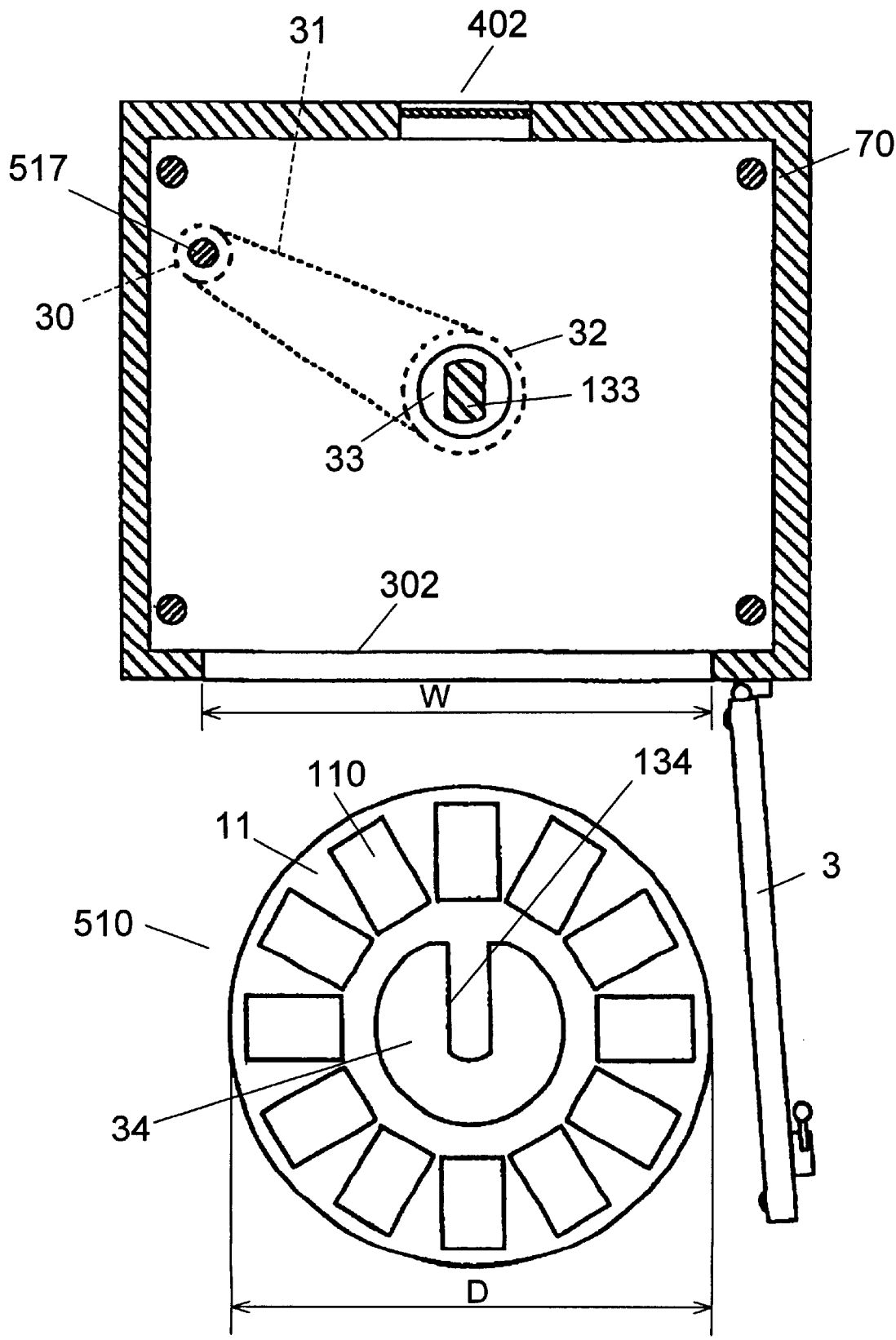

FIGS. 7 and 8 are plan cross sections of an incubator in accordance with the second exemplary embodiment.

Different from the first embodiment, a spline shaft is disposed outside the sample shelf so that the shelf can be removed with ease. An incubator used in the second embodiment includes a rotation driving mechanism and a lift driving mechanism for sample shelf as same as those of the first embodiment, and a control system also remains the same as that of the first embodiment, therefore, the descriptions are omitted here.

In FIG. 7, housing 70 has the same functions as housing 2 in the first embodiment. On a front face of housing 70, first opening 302 is provided and is opened or closed with first door 3. On a rear face of housing 70, second opening 402 with a shutter mechanism is provided. Sample shelf 510 comprising sample tables 11 is disposed in housing 70.

Housing 70 has second opening 402 on its rear face □ different from the first embodiment □ so that opening 402 is disposed at the place closest to receptors 110 rested on table 11 for the convenience of taking out or restoring the plate from/to the incubator. As shown in FIG. 8, a width (W) of first opening 302 is greater than a diameter (D) of table 11, thus if second opening 402 were disposed on a lateral face of housing 70, the second opening may be distant from receptor 110.

FIG. 9 is a lateral cross section taken on the lines D□ E□ F□ G□ H□ shown in FIG. 7.

In FIG. 9, an interior of housing 70 is partitioned into two spaces, i.e. first space S1 where lift member 518 lifted by feeder screw 13 which is rotated by a lift driving mechanism, and second space S2. Lift member 518 journals both of first rotating body 517 and second rotating body 33.

Through first rotating body 517, spline shaft 15 extends in a slidable manner. A lower end of shaft 15 is journaled by bearing 21 disposed on a base plate of housing 70. An upper section of shaft 15 protrudes into second space S2. Rotation of R-axis motor 20 is transmitted to rotating body 517 via pulley 22 coupled to motor 20, belt 23 and pulley 24 coupled to a tip of shaft 15. Rotation of rotating body 517 is transmitted to rotating body 33 via pulley 30 coupled to rotating body 517, pulley 32 coupled to rotating body 33 and belt 31 entrained on both the pulleys. Shelf 510 hung from rotating body 33 thus rotates. As such, a rotation driving mechanism, which rotates shelf 510 by spinning shaft 15, comprises motor 20, pulley 22, belt 23 and pulley 24.

Belt 31 functions as transmission member for transmitting the rotation of rotary body 517 to rotating body 33. Gears instead of the belt also can be used as the transmission member. Further, the transmission member can be omitted and rotary body 517 contacts with rotary body 33, which rotates rotary body 517 directly. In other words, rotation of rotating body 33 can be transmitted in any way to rotating body 517.

A lower section of rotating body 33 is flattened to form mating section 133, which mates with coupling plate 34 coupled to the upper most table 11 of shelf 510. As shown in FIG. 7 and FIG. 8, key-way 134 having a width corresponding to the width of mating section 133 is formed on coupling plate 34. Mating section 133 mates with key-way 134 so that shelf 510 can be held by rotating body 33 in a hanging manner.

Since there is no rotating shaft extending through shelf 510, shelf 510 can be removed/mounted simply by detaching/attaching coupling plate 34 from/to rotating body 33.

As shown in FIG. 8, the width (W) of first opening 302 of housing 70 is greater than the diameter (D) of table 11. Shelf 510 can be taken out and restored from/to housing 70 through opening 302. Shelf 510 can be removed from rotary body 33 by detaching mating section 133 from key-way 134. Shelf 510 can be thus taken out from housing 70 through opening 302 with ease. As a result, plates 6 are set on receptors 110 in an excellent operational condition, and maintenance work as well as cleaning of shelf 510 can be also practiced in the same good condition.

As discussed above, the incubator of the present invention is equipped with the rotation driving mechanism and lift driving mechanism for moving the sample shelf which holds a plurality of plates accommodating samples. The plates undergoing biochemical treatment can be thus taken out and restored from/to the incubator through the opening located at a specific place. Changes in environmental conditions inside the incubator can be restrained by minimizing the openings.

What is claimed is:

1. An incubator comprising:
   (a) a housing;
   (b) a sample shelf disposed in said housing and holding at least one plate accommodating a sample, said shelf being removable from said housing;
   (c) a controller for maintaining an environment in said housing at a given condition;
   (d) a first opening provided on said housing, said first opening being sized such that said shelf is insertable and removable from said housing through said first opening;
   (e) a first door for closing said first opening;
   (f) a second opening provided on said housing and having a size smaller than said first opening yet large enough for at least said one plate to pass through, said plate being inserted or removed from said housing through said second opening;
   (g) a second door for closing said second opening; and
   (h) a driving mechanism for closing and opening said second door.

2. An incubator comprising:
   (a) a housing;
   (b) a sample shelf disposed in said housing and holding at least one plate accommodating a sample, said shelf being equipped with a plurality of sample tables vertically assembled and able to wheel in a plane within said housing,
   (c) a controller for maintaining an environment in said housing at a given condition;
   (d) a first opening provided on said housing;
   (e) a first door for closing said first opening;
   (f) a second opening provided on said housing and having a size smaller than said first opening yet large enough for at least one plate to pass through; and
   (g) a second door for closing said second opening.

3. The incubator as defined in claim 2 further comprising a transfer mechanism which moves said shelf within said housing for positioning said plate to be taken out from said housing through said second opening.

4. The incubator as defined in claim 3 further comprising a controller which controls said transfer mechanism for at least one of positioning said plate with regard to said second opening and moving said shelf to agitate atmosphere inside said housing.

5. The incubator as defined in claim 2 further comprising:
   a rotating body coupled to said shelf and wheeling together with said shelf;
   a lift member for journaling said rotating body;
   a feed screw for raising and lowering said lift member;
   a lift driving mechanism for rotating said feed screw;
   a spline shaft extending through said rotating body in a slidable manner; and
   a rotation driving mechanism which rotates said shelf by rotating said spline shaft.

6. The incubator as defined in claim 5 further comprising:
   a floor for partitioning an interior of said housing into a first space and a second space;
   wherein the first space includes said shelf, said rotating body, said lift member, said feed screw and said spline shaft,
   wherein the second space includes said lift driving mechanism and said rotation driving mechanism; and
   wherein said feed screw is engaged with said lift driving mechanism and said spline shaft is engaged with said rotation driving mechanism via respective shaft holes provided on said floor.

7. The incubator as defined in claim 2 further comprising:
   a first rotating body;
   a second rotating body coupled to said shelf and wheeling together with said shelf;
   a lift member journaling both said first rotating body and said second rotating body;
   a feed screw for raising and lowering said lift member;
   a lift driving mechanism for rotating said feed screw;
   a spline shaft extending through said first rotating body in a slidable manner and transmitting rotation of said spline shaft to said first rotating body;
   a transmission mechanism for transmitting rotation of said first rotating body to said second rotating body; and
   a rotation driving mechanism which rotates said shelf by rotating said spline shaft.

8. The incubator as defined in claim 7 further comprising:
   a floor for partitioning an interior of said housing into a first space and a second space,
   wherein the first space includes said shelf, said first rotating body, said second rotating body, said lift member, said feed screw and said spline shaft,
   wherein the second space includes said lift driving mechanism and said rotation driving mechanism; and
   wherein said feed screw is engaged with said lift driving mechanism and said spline shaft is engaged with said rotation driving mechanism via respective shaft holes provided on said floor.

9. The incubator as defined in claim 2 further comprising:
   a rotating body coupled to said shelf and wheeling together with said shelf;
   a lift member for journaling said rotating body;
   a lift driving mechanism raising and lowering said lift member;
   a shaft extending through said rotating body in a slidable manner; and
   a rotation driving mechanism which rotates said shelf by rotating said shaft.

10. The incubator as defined in claim 2 further comprising:
    a first rotating body;
    a second rotating body coupled to said shelf and wheeling together with said shelf;
    a lift member journaling both said first rotating body and said second rotating body;
    a lift driving mechanism for raising and lowering said lift member;
    a shaft extending through said first rotating body in a slidable manner and transmitting rotation of said shaft to said first rotating body;
    a transmission mechanism for transmitting rotation of said first rotating body to said second rotating body; and
    a rotation driving mechanism which rotates said shelf by rotating said shaft.

11. An incubator according to claim 1, wherein said plate is inserted or removed from said housing through said second opening by a robotic mechanism.

* * * * *